United States Patent
Leleti et al.

(10) Patent No.: US 11,279,672 B2
(45) Date of Patent: Mar. 22, 2022

(54) ASYMMETRIC SYNTHESIS OF ALPHA-BRANCHED CHIRAL AMINES

(71) Applicant: PIRAMAL PHARMA LIMITED, Maharashtra (IN)

(72) Inventors: Rajender Reddy Leleti, Gujarat (IN); Sharadsrikar Kotturi, Gujarat (IN); Yogesh Waman, Gujarat (IN); Chirag Patel, Gujarat (IN); Aditya Patwa, Gujarat (IN); Rajesh Shenoy, Gujarat (IN)

(73) Assignee: PIRAMAL PHARMA LIMITED, Mumbai (IN)

( * ) Notice: Subject to any disclaimer, the term of this patent is extended or adjusted under 35 U.S.C. 154(b) by 13 days.

(21) Appl. No.: 17/041,133

(22) PCT Filed: Apr. 17, 2019

(86) PCT No.: PCT/IB2019/053161
§ 371 (c)(1),
(2) Date: Sep. 24, 2020

(87) PCT Pub. No.: WO2019/202522
PCT Pub. Date: Feb. 4, 2019

(65) Prior Publication Data
US 2021/0114977 A1   Apr. 22, 2021

(30) Foreign Application Priority Data

Apr. 18, 2018 (IN) .............................. 201821014706

(51) Int. Cl.
| | |
|---|---|
| *C07C 303/40* | (2006.01) |
| *C07C 213/02* | (2006.01) |
| *C07B 53/00* | (2006.01) |
| *C07C 217/58* | (2006.01) |
| *C07C 217/60* | (2006.01) |
| *C07C 311/13* | (2006.01) |

(52) U.S. Cl.
CPC .......... *C07C 303/40* (2013.01); *C07C 213/02* (2013.01); *C07B 53/00* (2013.01); *C07B 2200/07* (2013.01); *C07C 217/58* (2013.01); *C07C 217/60* (2013.01); *C07C 311/13* (2013.01)

(58) Field of Classification Search
None
See application file for complete search history.

(56) References Cited

U.S. PATENT DOCUMENTS

2014/0171639 A1*   6/2014   Biswas ................... A61P 11/00
544/91

OTHER PUBLICATIONS

ISR for International Application PCT/IB2019/053161, (2019).
Written Opinion for International ApplicationPCT/IB2019/053161, (2019).
D. A. Cogan, et al.: "Asymmetric synthesis of a, a-dibranched amines by the Trimethyl-aluminum-mediated 1, 2-addition of organolithiums to tert-butanesulfinyl ketimines," Journal of the American Chemical Society, 1999, 121(1), pp. 268-269. Title; abstract; p. 269, Table 2;p. 269, reaction (3); (1999).
D. W. Slocum, et al.: "Directed metalation reactions. 6. Competition of substituents for ortho direction of metalation in substituted anisoles," The Journal of Organic Chemistry, 1976, 41(23), pp. 3653-3664. Abstract; p. 3653. Second paragraph; p. 3654, Table I; p. 3658, equation(3), (1976).
T. Kremer, et al., "Mechanisms of competitive ring-directed and side-chain-directed metalations in ortho-substituted toluenes," Organometallics, 1996, 15(15), pp. 3345-3359. Title; abstract; p. 3354, right-hand column; p. 3357, 42, Cs; p. 3350, 15, C1; p. 3359, left-hand column, (1996).
V. Y. Rodriguez, et al., "Directed ortho-lithiation of unprotected diphenylphosphinic acids," Tetrahedron, 2012, 68(36), pp. 7355-7362. Abstract;p. 7356, Table I, entries 6 and 7; p. 7355, Scheme 1, (2012).
H. A. Rajapakse, et al., "Asymmetric synthesis of dihydroquinazolinones via directed ortho metalation and addition to tert-butanesulfinyl imines." Tetrahedron letters, 2005, 46(51), pp. 8909-8912. Abstract; p. 8910, Table 1, (2005).
Liang Cheng, et al., "Highly diastereoselective reactions of 2-lithiated indoles with chiral N-tert-butanesulfinyl aldimines for the synthesis of chiral (2-indolyl) methanamine derivatives," Tetrahedron: Asymmetry, 2007, 18(15), p. 1833-1843. Title, abstract; p. 1834, Scheme 1, (2007).

* cited by examiner

*Primary Examiner* — Sudhakar Katakam
*Assistant Examiner* — Jennifer C Sawyer
(74) *Attorney, Agent, or Firm* — Ladas & Parry LLP

(57) ABSTRACT

The present invention relates to an improved asymmetric synthesis of alpha-branched amines (hereafter referred to as the compound) and relative chiral amines (1") or its pharmaceutically acceptable salt and derivatives. The process comprises an unusual substrate specific regioselective ortho lithiation of substituted arene compounds, followed by its highly diastereoselective addition to N-tert-butanesulfinylimines resulting in the selective formation of alpha-branched sulfinyl amine and chiral amine; which on subsequently removing the sulfinyl group provides corresponding alpha-branched amines or relative chiral amines (1").

4 Claims, No Drawings

ASYMMETRIC SYNTHESIS OF ALPHA-BRANCHED CHIRAL AMINES

RELATED APPLICATION

This application is an application under 35 U.S.C. 371 of International Application No. PCT/IB2019/053161 filed on 17 Apr. 2019, which claims priority from Indian Application No. 201821014706 filed 18 Apr. 2018, the disclosures of which are incorporated in their entirety by reference herein.

FIELD OF THE INVENTION

The present invention relates to an improved asymmetric synthesis of alpha-branched amines (hereafter referred to as the compound (1)) and relative chiral amines (1″) or its pharmaceutically acceptable salts and derivatives; through the formation of intermediate compounds with lithium-cycles.

BACKGROUND OF THE INVENTION

The following discussion of the prior art is intended to present the invention in an appropriate technical context, and allows its significance to be properly appreciated. Unless clearly indicated to the contrary, reference to any prior art in this specification should not be construed as an expressed or implied admission that such art is widely known or forms part of common general knowledge in the field.

The compounds of formula (1), alpha-branched chiral amines and relative chiral amines compound (1″) are ubiquitous structural motifs present in many drugs, investigational drug candidates, bioactive substances as well as natural products; such as O-methylbharatamine, compound DPC-961, compound (±)SM-15811 and so on. The compounds of formula (1) and (1″) are also effectively used in asymmetric synthesis of chiral polydentate ligands. The compounds of formula (1), alpha-branched amines and amine compound (1″) are structurally represented as follows;

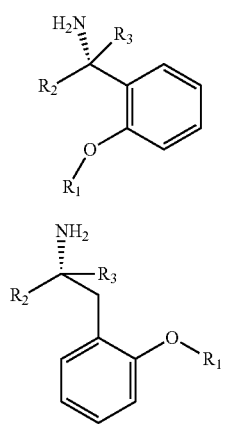

wherein, $R_1$, $R_2$ and $R_3$ is independently selected from H, $C_1$-$C_{10}$ linear or branched or cyclic alkyl, substituted or unsubstituted aryl, ester, ether, hetero aryl, halo, haloalkyl.

The amine compounds of formula (1) and (1″) being important intermediates for several bioactive compounds; a number of processes for its preparation are known in the art.

The journal article Tetrahedron Letters 46, p 8909-8912 (2005) disclosed the asymmetric synthesis of dihydroquinazolinones via directed ortho-metalation of N-Boc anilines using s-BuLi and addition to tert-butanesulfinyl imines as depicted below; wherein the product obtained with very low diastereoselectivity ratio and with poor yield.

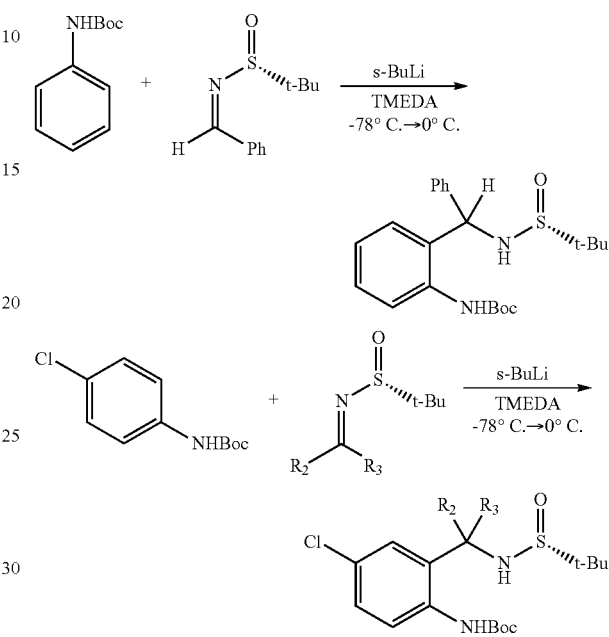

The journal article Tetrahedron: Asymmetry 18, p 2910-2914 (2007) disclosed the diastereoselective Pomeranz-Fritsch-Bobbitt synthesis of (S)-(−)-O-methylbharatamine using (S)—N-tert-butanesulfinimine as a substrate; wherein the addition of lithiated N,N-diethyl-o-toluamide to the sulfinimine C═N double bond was the key step of the synthesis. The amide carbanion was generated with t-BuLi at −72° C. affording the sulfinyl compound as an oil. The article further disclosed that the diastereoselectivity of this step could not be established either by chiral HPLC analysis, run under various conditions, or by $^1$H NMR spectroscopy. Accordingly, the N-sulfinyl auxiliary was removed from sulfinyl amide compound using concentrated hydrochloric acid in methanol, as depicted below:

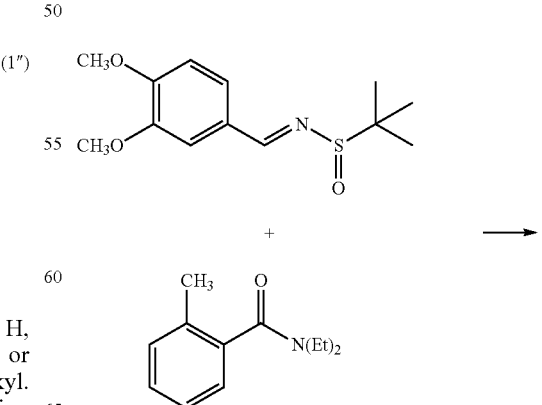

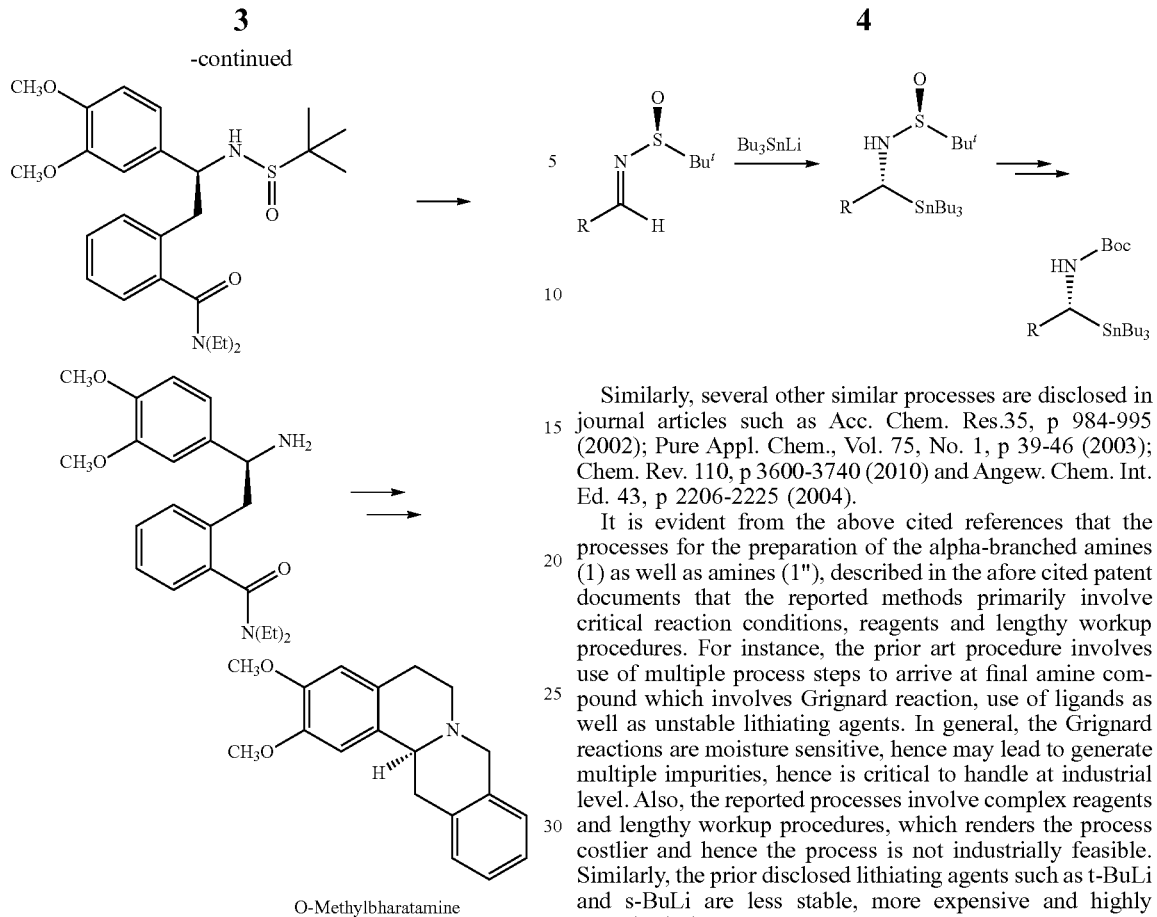

O-Methylbharatamine

The journal article Tetrahedron: Asymmetry 13, p 303-310 (2002) disclosed the asymmetric synthesis of diarylmethylamines by diastereoselective addition of organometallic reagents to chiral N-tert-butanesulfinimines as depicted below; wherein the sulfinyl compound was obtained with very low diastereoselectivity ratio.

The journal article ORGANIC LETTERS, Vol. 5, No. 22, p 4215-4218 (2003) disclosed the synthesis of chiral, non-racemic alpha-aminoorganostannanes by addition of Bu₃SnLi to tert-Butanesulfinimines; wherein the adducts are readily converted to enantiomerically enriched N-Boc-protected alpha-aminoorganostannanes.

Similarly, several other similar processes are disclosed in journal articles such as Acc. Chem. Res.35, p 984-995 (2002); Pure Appl. Chem., Vol. 75, No. 1, p 39-46 (2003); Chem. Rev. 110, p 3600-3740 (2010) and Angew. Chem. Int. Ed. 43, p 2206-2225 (2004).

It is evident from the above cited references that the processes for the preparation of the alpha-branched amines (1) as well as amines (1"), described in the afore cited patent documents that the reported methods primarily involve critical reaction conditions, reagents and lengthy workup procedures. For instance, the prior art procedure involves use of multiple process steps to arrive at final amine compound which involves Grignard reaction, use of ligands as well as unstable lithiating agents. In general, the Grignard reactions are moisture sensitive, hence may lead to generate multiple impurities, hence is critical to handle at industrial level. Also, the reported processes involve complex reagents and lengthy workup procedures, which renders the process costlier and hence the process is not industrially feasible. Similarly, the prior disclosed lithiating agents such as t-BuLi and s-BuLi are less stable, more expensive and highly pyrophoric in nature.

In view of these drawbacks, there is a need to develop an industrially viable commercial process for the preparation of the compounds of formula (1) and compound (1"); which is simple, efficient and cost-effective process and provides the desired compounds in improved yield and purity.

Inventors of the present invention have developed an improved process that addresses the problems associated with the processes reported in the prior art. The inventors of the instant invention reasoned that a direct method to access enantio-enriched alpha-branched amines (1) as well as amines (1"), would be an asymmetric addition of relative substituted arene anion to Ellman's Imines, which has not been explicitly reported in the art on the currently considered chemical moieties. These reaction conditions, however, surprisingly led to an unusual substrate specific regioselective lithiation of arene compounds. The inventors envisages that these synthetic effort could be of value in a variety of research applications, including the discovery of the known as well as new bioactive substances, and also can be extended to broad substrate scope. The process of the present invention does not involve use of any toxic, critical and/or costly catalysts, solvents and reagents. Moreover, the process does not require additional purification and critical crystallization procedure. Accordingly, the present invention provides a process for the preparation of the alpha-branched amines (1) as well as amines (1") and its intermediates; which is simple, efficient, cost effective, environmentally friendly and commercially scalable for large scale operations.

SUMMARY OF THE INVENTION

In one aspect, the present invention relates to an improved process for the preparation of alpha-branched amine (1)

comprising, reacting cyclic lithiated compound (2-Li) with N-tert-butanesulfinylimine (3) to produce alpha-branched sulfinyl amine (4); and subsequently removing the sulfinyl group.

In one aspect, the present invention relates to an improved process for the preparation of alpha-branched sulfinyl amine (4) comprising, reacting cyclic lithiated compound (2-Li) with N-tert-butanesulfinylimine (3).

In one aspect, the present invention relates to an improved process for the preparation of alpha-branched amine (1) comprising.

(a) reacting substituted arene (2) with N-tert-butanesulfinylimine (3) in the presence of lithiating agent;
(b) removing the sulfinyl group from the compound alpha-branched sulfinyl amine (4) of stage (a).

In one aspect, the present invention relates to an improved process for the preparation of branched amine (1") comprising, reacting cyclic lithiated compound (5-Li) with N-tert-butanesulfinylimine (3) to produce branched sulfinyl amine (6); and subsequently removing the sulfinyl group.

In one aspect, the present invention relates to an improved process for the preparation of branched sulfinyl amine (6) comprising, reacting cyclic lithiated compound (5-Li) with N-tert-butanesulfinylimine (3).

In one aspect, the present invention relates to an improved process for the preparation of branched amine (1") comprising, (x) reacting substituted arene (5) with N-tert-butanesulfinylimine (3) in the presence of lithiating agent;
(y) removing the sulfinyl group from the compound branched sulfinyl amine (6) of stage (x).

DETAILED DESCRIPTION OF THE INVENTION

Accordingly, the present invention relates to an improved process for the preparation of alpha-branched amine (1) or its salts, represented by the following formula,

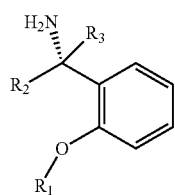
(1)

wherein, $R_1$, $R_2$ and $R_3$ is independently selected from H, $C_1$-$C_{10}$ linear or branched or cyclic alkyl, substituted or unsubstituted aryl, ester, ether hetero aryl, halo, haloalkyl comprising the steps of;

(a) reacting substituted arene compound (2) represented by the following formula,

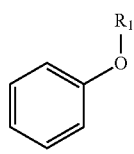
(2)

with N-tert-butanesulfinylimine compound (3) represented by the following formula,

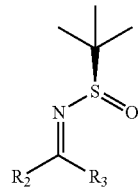
(3)

in the presence of a lithiating agent;

(b) removing the sulfinyl group from the compound alpha-branched sulfinyl amine compound (4) of stage (a) represented by the following formula,

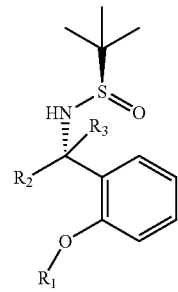
(4)

The compound (1) obtained by the afore described process is optionally converted into various therapeutically active drugs or advanced drug intermediates.

In an embodiment, the lithiating agent used at step (a) is an organolithium compound selected from n-butyl lithium (n-BuLi), phenyllithium, methyllithium, tert-butyllithium or mixture thereof.

In an embodiment, the lithiating agent used is n-Butyl Lithium (n-BuLi). Accordingly, the present invention relates to an improved process for the preparation of alpha-branched sulfinyl amine compound (4) represented by the following formula,

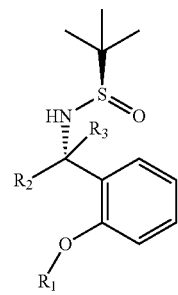
(4)

wherein, $R_1$, $R_2$ and $R_3$ is independently selected from H, $C_1$-$C_{10}$ linear or branched or cyclic alkyl, substituted or unsubstituted aryl, ester, ether, hetero aryl, halo, haloalkyl comprising, reacting cyclic lithiated compound (2-Li) represented by the following formula,

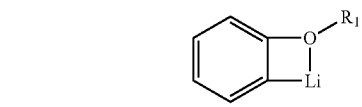

with N-tert-butanesulfinylimine compound (3) represented by the following formula,

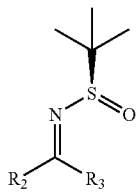

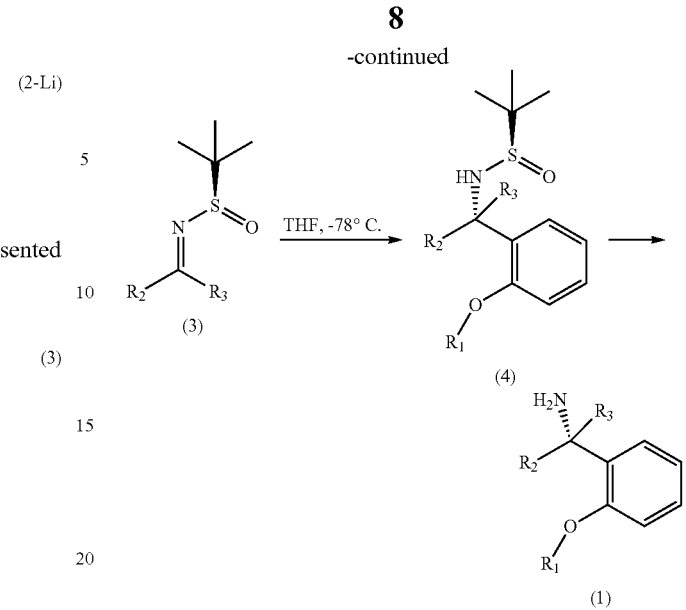

The compound (4) obtained by the afore described process is optionally converted into alpha-branched amine (1) by removing the sulfinyl group from the compound alpha-branched sulfinyl amine (4).

In the context of the present invention, the term "optionally" when used in reference to any element; including a process step e.g. optionally converted; it is intended to mean that the subject compound is subsequently converted, or alternatively, is not converted into the compound (1). Both alternatives are intended to be within the scope of the present invention.

In a specific embodiment, the process for the preparation of alpha-branched amine (1) comprises the steps of;

(i) dissolving substituted arene compound (2) in a solvent;

(ii) cooling the reaction mixture of stage (i) to a temperature of about 0° C.;

(iii) adding n-Butyl Lithium (n-BuLi) to the stirring solution of stage (ii);

(iv) cooling the reaction mixture of stage (iii) to a temperature of about −78° C.;

(v) adding N-tert-butanesulfinylimine (3) to the stirring solution of stage (iv);

(vi) stirring the reaction mixture of stage (v) at a temperature of about −78° C.;

(vii) isolating the alpha-branched sulfinyl amine compound (4);

(viii) removing the sulfinyl group.

The process of the present invention as per the specific embodiment described above is illustrated in the following Scheme (A);

Scheme-(A)

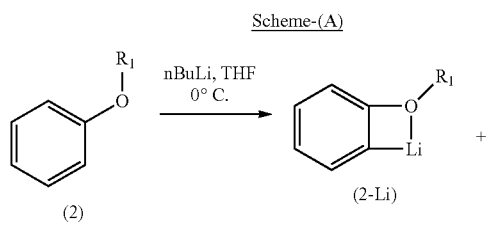

wherein, $R_1$, $R_2$ and $R_3$ is independently selected from H, $C_1$-$C_{10}$ linear or branched or cyclic alkyl, substituted or unsubstituted aryl, ester, ether, hetero aryl, halo, haloalkyl.

The solvent used in any of the process steps from the step (i) to step (viii) of the above process (as depicted in the Scheme (A)) is selected from an ether solvent such as tetrahydrofuran, cyclopentyl methyl ether, 2-methyltetrahydrofuran, diethyl ether, dioxane, 1,4-dioxane, 1,2-dioxane and 1,3-dioxane; an alcoholic solvent such as methanol, ethanol, isopropanol, t-amyl alcohol, t-butyl alcohol and hexanol; halogenated solvent such as dichloromethane, 4-bromotoluene, diiodomethane, carbon tetrachloride, chlorobenzene and chloroform; ketone such as acetone; an aprotic solvent such as acetonitrile, N,N-dimethyl formamide (DMF), N,N-dimethyl acetamide, dimethyl sulfoxide (DMSO) and N-methylpyrrolidone (NMP); an aromatic solvent such as toluene, xylene and benzene; water or a mixture thereof.

The term 'temperature of about 0° C.' referred to in the step (ii) of the above process (as depicted in the Scheme (A)) can range from −5° C. to +5° C.

The term 'temperature of about −78° C.' referred to in the step (iv) or (vi) of the above process (as depicted in the Scheme (A)) can range from −70° C. to −90° C.

The term 'isolating' the compound referred to in any process step from step (i) to step (viii) corresponds to the isolating or separating the obtained product using methods that corresponds to the steps involving addition of water, biphasic solvent workup, separation of solvent layers or precipitation, evaporation of solvent, filtration, washing and drying.

The term 'removing the sulfinyl group' the compound referred to in any process step (viii) corresponds to the cleaving of the sulfinyl substitution of the amine and producing the free amine compound. The removal of the sulfinyl group is achieved by treatment of the compound (4) with an acid, for example hydrochloric acid, hydrobromic acid, hydrofluoric acid, nitric acid, sulfuric acid, phosphoric acid or mixture thereof.

The inventors of the instant invention reasoned that a direct method to access alpha-branched amine would be an asymmetric synthesis comprising direct ortho lithiation of anisoles and similar relative substituted arene compounds followed by addition to the Ellman's Imines, which has not been explicitly reported in the art on the currently considered chemical moieties. These reaction conditions, however, surprisingly led to an unusual substrate specific regioselective lithiation of substituted arene compounds such as anisole, involves formation of compounds with Lithiumcycles. The inventors envisages that these synthetic effort could be of value in a variety of research applications, including the discovery of the known as well as new bioactive substances; many drugs, investigational drug candidates, and natural products and so on.

The process of the present invention as per the specific embodiment described above is illustrated in the following Scheme (B);

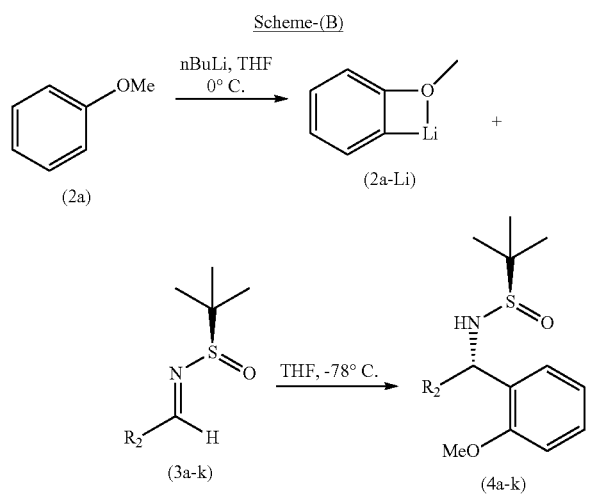

wherein $R_2$ represents variable as listed in below Table-1.

In the representative case illustrated below wherein the addition of anisole (2a-Li) lithiumcycle to various N-tert-Butanesulfinyl aldimines (3a-k) was studied. For instance, the reaction of 3a-k with lithiumcycle (2a-Li) in THF at −78° C. for 2 h afforded alpha-branched sulfinyl amine (4a-k) in about 92% yield and with a high diasteromeric ratio (dr 98:2). The diastereoselectivity of the reaction was determined to be 98:2 by $^1$H NMR analysis. The obtained compound (4a-k) was further treated with hydrochloric acid to remove the sulfinyl group.

TABLE 1

Diastereoselective addition of ortho-lithiated anisole (lithiumcycle) (2a-Li) to various N-tert-Butanesulfinyl Aldimines[a]

| Substrate ($R_2$) | product | yield (%)[b] | dr[c] |
|---|---|---|---|
| 3a: $R_2$ = Ph | 4a | 90 | >95:5 |
| 3b: $R_2$ = o-ClC$_6$H$_5$ | 4b | 91 | >95:5 |
| 3c: $R_2$ = p-MeC$_6$H$_5$ | 4c | 90 | >95:5 |
| 3d: $R_2$ = p-MeoC$_6$H$_5$ | 4d | 89 | >95:5 |
| 3e: $R_2$ = 2-Furyl | 4e | 90 | >95:5 |
| 3f: $R_2$ = 2-Thiophenyl | 4f | 92 | >95:5 |
| 3g: $R_2$ = Cinnamyl | 4g | 82 | 90:10 |
| 3h: $R_2$ = 3-ph-propionyl | 4h | 85 | 90:10 |
| 3i: $R_2$ = Isopropyl | 4i | 88 | >98:2 |
| 3j: $R_2$ = Isovaleryl | 4j | 84 | 92:8 |
| 3k: $R_2$ = n-Butyl | 4k | 80 | 91:9 |

[a]All the reactions performed with 1.0 equiv of 3 and 5.0 equiv of 2a and n-BuLi (3.0 equiv)at 0 to −78° C. for 2 h, unless stated otherwise indicate;

TABLE 1-continued

Diastereoselective addition of ortho-lithiated anisole (lithiumcycle) (2a-Li) to various N-tert-Butanesulfinyl Aldimines[a]

| Substrate ($R_2$) | product | yield (%)[b] | dr[c] |
|---|---|---|---|

[b]Isolated yield;
[c]The diastereoselectivity was determined by $^1$H NMR analysis. The ">95:5" dr denotes that signal for only one diastereomer were observed In another embodiment, there is provided an improved process for the preparation of branched amine (1''') comprising, reacting cyclic lithiated compound (5-Li) with N-tert-butanesulfinylimine (3) to produce branched sulfinyl amine (6); and subsequently removing the sulfinyl group.

In a further embodiment, there is provided an improved process for the preparation of branched sulfinyl amine (6) comprising, reacting cyclic lithiated compound (5-Li) with N-tert-butanesulfinylimine (3).

Accordingly, the present invention relates to an improved process for the preparation of a branched amine compound (1''') or its salts, represented by the following formula,

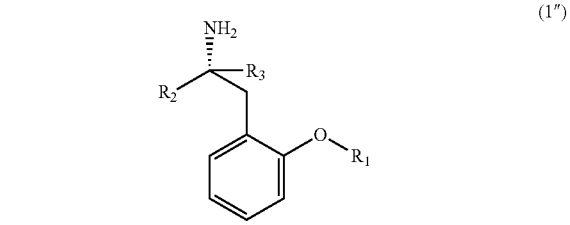

wherein, $R_1$, $R_2$ and $R_3$ is independently selected from H, $C_1$-$C_{10}$ linear or branched or cyclic alkyl, substituted or unsubstituted aryl, ester, ether, hetero aryl, halo, haloalkyl comprising the steps of;

(x) reacting substituted arene compound (5) represented by the following formula,

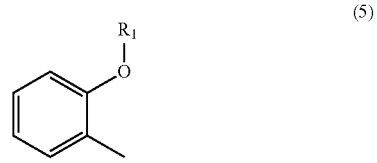

with N-tert-butanesulfinylimine compound (3) represented by the following formula,

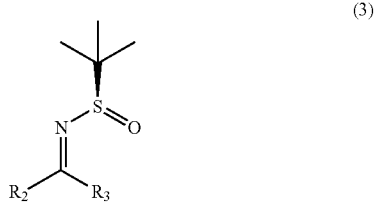

in the presence of a lithiating agent;

(y) removing the sulfinyl group from the compound sulfinyl amine (6) of stage (x) represented by the following formula,

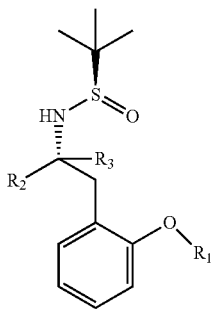

(6)

The compound (1″) obtained by the afore described process is optionally converted into various therapeutically active drugs or advanced drug intermediates.

In an embodiment, the lithiating agent used is n-Butyl Lithium (n-BuLi). Accordingly, the present invention relates to an improved process for the preparation of branched sulfinyl amine compound (6) represented by the following formula,

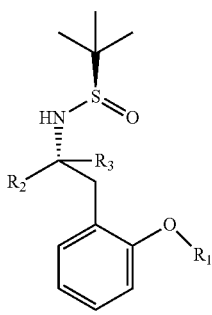

(6)

wherein, $R_1$, $R_2$ and $R_3$ is independently selected from H, $C_1$-$C_{10}$ linear or branched or cyclic alkyl, substituted or unsubstituted Aryl, ester, ether, hetero aryl, halo, haloalkyl comprising, reacting cyclic lithiated compound (5-Li) represented by the following formula,

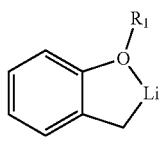

(5-Li)

with N-tert-butanesulfinylimine compound (3) represented by the following formula,

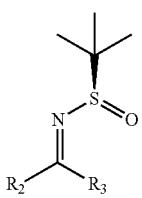

(3)

The compound (6) obtained by the afore described process is optionally converted into branched amine (1″) by removing the sulfinyl group from the compound branched sulfinyl amine (6).

In the context of the present invention, the term "optionally" when used in reference to any element; including a process step e.g. optionally converted; it is intended to mean that the subject compound is subsequently converted, or alternatively, is not converted into the compound (1″). Both alternatives are intended to be within the scope of the present invention.

In a specific embodiment, the process for the preparation of a chiral amine compound (1″) comprises the steps of;

(xi) dissolving substituted arene compound (5) in a solvent;

(xii) cooling the reaction mixture of stage (xi) to a temperature of about 0° C.;

(xiii) adding n-Butyl Lithium (n-BuLi) to the stirring solution of stage (xii);

(xiv) cooling the reaction mixture of stage (xiii) to a temperature of about −78° C.;

(xv) adding N-tert-butanesulfinylimine (3) to the stirring solution of stage (xiv);

(xvi) stirring the reaction mixture of stage (xv) at a temperature of about −78° C.;

(xvii) isolating the sulfinyl amine compound (6);

(xviii) removing the sulfinyl group.

The process of the present invention as per the specific embodiment described above is illustrated in the following Scheme (C);

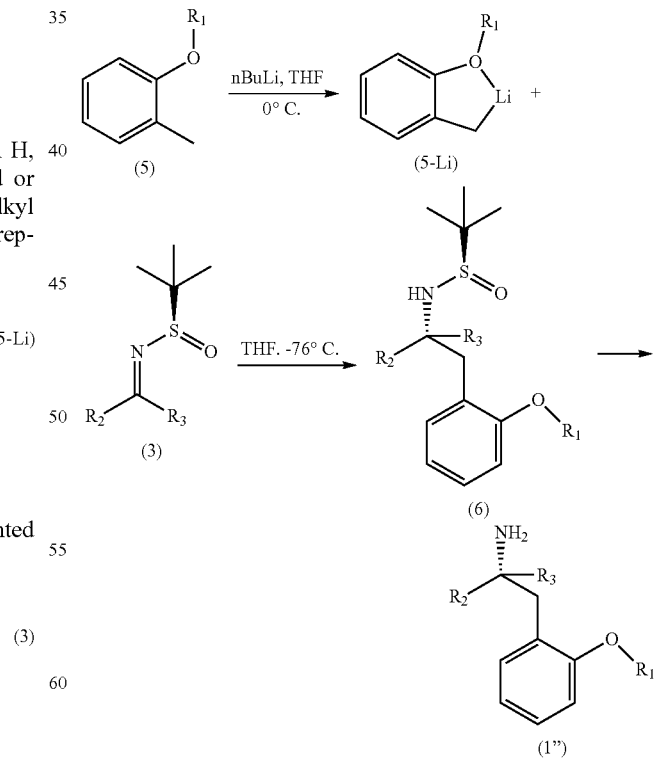

Scheme-(C)

wherein, $R_1$, $R_2$ and $R_3$ is independently selected from H, $C_1$-$C_{10}$ linear or branched or cyclic alkyl, substituted or unsubstituted aryl, ester, ether, hetero aryl, halo, haloalkyl.

The solvent used in any of the process steps from the step (xi) to step (xviii) of the above process (as depicted in the Scheme (C)) is selected from an ether solvent such as tetrahydrofuran, cyclopentyl methyl ether, 2-methyltetrahydrofuran, diethyl ether, dioxane, 1,4-dioxane, 1,2-dioxane and 1,3-dioxane; an alcoholic solvent such as methanol, ethanol, isopropanol, t-amyl alcohol, t-butyl alcohol and hexanol; halogenated solvent such as dichloromethane, 4-bromotoluene, diiodomethane, carbon tetrachloride, chlorobenzene and chloroform; ketone such as acetone; an aprotic solvent such as acetonitrile, N,N-dimethyl formamide (DMF), N,N-dimethyl acetamide, dimethyl sulfoxide (DMSO) and N-methylpyrrolidone (NMP); an aromatic solvent such as toluene, xylene and benzene; water or a mixture thereof.

The term 'temperature of about 0° C.' referred to in the step (xii) of the above process (as depicted in the Scheme (C)) can range from −5° C. to +5° C.

The term 'temperature of about −78° C.' referred to in the step (xiv) or (xvi) of the above process (as depicted in the Scheme (C)) can range from −70° C. to −90° C.

The term 'isolating' the compound referred to in any process step from step (xi) to step (xviii) corresponds to the isolating or separating the obtained product using methods that corresponds to the steps involving addition of water, biphasic solvent workup, separation of solvent layers or precipitation, evaporation of solvent, filtration, washing and drying.

The term 'removing the sulfinyl group' the compound referred to in any process step (xviii) corresponds to the cleaving of the sulfinyl substitution of the amine and producing the free amine compound. The removal of the sulfinyl group is achieved by treatment of the compound (5) with an acid, for example hydrochloric acid, hydrobromic acid, hydrofluoric acid, nitric acid, sulfuric acid, phosphoric acid or a mixture thereof.

The process of the present invention as per the specific embodiment described above is illustrated in the following Scheme (D);

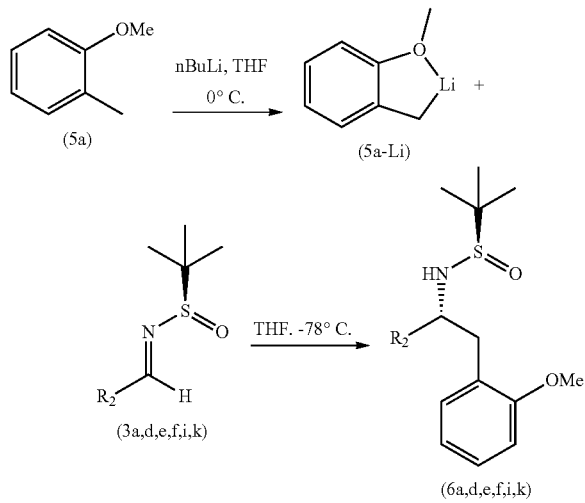

wherein $R_2$ represents variable as listed in below Table-2.

In the representative case illustrated below wherein the addition of anisole (5a-Li) lithiumcycle to various N-tert-Butanesulfinyl aldimines (3a,d,e,f,I,k) was studied. For instance, the reaction of 3a,d,e,f,I,k with lithiumcycle (5a-Li) in THF at −78° C. for 2 h afforded branched sulfinyl amine (6a,d,e,f,I,k) in about 90% yield and with a high diastereomeric ratio (dr 98:2). The diastereoselectivity of the reaction was determined to be 95:5 by $^1$H NMR analysis. The obtained compound (6a,d,e,f,I,k) was further treated with hydrochloric acid to remove the sulfinyl group.

TABLE 2

Diastereoselective addition of lithiated ortho-methylanisole (lithiumcycle) (5a-Li) to various N-tert-Butanesulfinyl Aldimines[a]

| Substrate ($R_2$) | product | yield (%)[b] | dr[c] |
| --- | --- | --- | --- |
| 3a: $R_2$ = Ph | 6a | 86 | >95:5 |
| 3d: $R_2$ = p-MeoC$_6$H$_5$ | 6d | 90 | >94:6 |
| 3e: $R_2$ = 2-Furyl | 6e | 85 | >93:7 |
| 3f: $R_2$ = 2-Thiophenyl | 6f | 88 | >93:7 |
| 3i: $R_2$ = Isopropyl | 6i | 90 | >95:5 |
| 3k: $R_2$ = n-Butyl | 6k | 80 | 90:10 |

[a]All the reactions performed with 1.0 equiv of 3 and 5.0 equiv of 2a and n-BuLi (3.0 equiv) at 0 to −78° C. for 2 h, unless stated otherwise indicate;
[b]Isolated yield;
[c]The diastereoselectivity was determined by $^1$H NMR analysis. The ">95:5" dr denotes that signal for only one diastereomer were observed It is evident that, the instantly presented invention is an unusual substrate specific regioselective lithiation of arene compounds with the formation of Lithiumcycles, and followed by highly diastereoselective addition to N-tert-butanesulfinylimines resulting in the selective formation of chiral amines (4) and (6) and further converted to corresponding amine (1) and (1″) respectively.

Advantageously, the above identified elements of the process of the instant invention effectively contribute to the reduction of overall cost of the process.

The invention is further illustrated by the following examples which are provided to be exemplary of the invention, and do not limit the scope of the invention. While the present invention has been described in terms of its specific embodiments, certain modifications and equivalents will be apparent to those skilled in the art and are intended to be included within the scope of the present invention.

EXAMPLES

Example-1: (R)—N—((S)-(2-methoxyphenyl)(phenyl)methyl)-2-methylpropane-2-sulfinamide (4a)

Charged 2.5 mL of tetrahydrofuran (THF) in a flask followed by the addition of anisole (2a) (5.0 mmol) and n-butyl lithium (1.6 M in cyclohexane, 3 mmol) at a temperature of about 0° C. The reaction mixture was further cooled down to a temperature of about −78° C. and to the stirring solution was added N-tert-butanesulfinyl aldimine (3a) (200 mg, 0.96 mmol). The reaction mixture was continued for stirring for about 2 h at −78° C. temperature; followed by the dropwise addition of water (5 mL) at same temperature. The reaction mixture was extracted with ethyl acetate (5 mL×3) and the separated organic layer was evaporated to provide compound (4a) with yield (273 mg, 90%).

Example-2: (R)—N—((R)-(2-chlorophenyl)(2-methoxyphenyl)methyl)-2-methylpropane-2-sulfinamide (4b)

Charged 2.5 mL of tetrahydrofuran (THF) in a flask followed by the addition of anisole (2a) (5.0 mmol) and n-butyl lithium (1.6 M in cyclohexane, 3 mmol) at a temperature of about 0° C. The reaction mixture was further cooled down to a temperature of about −78° C. and to the stirring solution was added N-tert-butanesulfinyl aldimine (3b) (200 mg, 0.82 mmol). The reaction mixture was continued for stirring for about 2 h at −78° C. temperature; followed by the dropwise addition of water (5 mL) at same temperature. The reaction mixture was extracted with ethyl acetate (5 mL×3) and the separated organic layer was evaporated to provide compound (4b) with yield (262 mg, 91%).

Example-3: (S)-(2-Methoxyphenyl)(Phenyl)Methanamine (1a)

Charged 0.7 mL of Dioxane in a flask followed by the addition of (R)—N—((S)-(2-methoxyphenyl)(phenyl)methyl)-2-methylpropane-2-sulfinamide (4a) (100 mg, 0.28 mmol) and hydrochloric acid solution (4.0 M in dioxane, 2.8 mmol, 0.7 mL). The reaction mixture was stirred for 2 h at room temperature and the reaction mixture was concentrated under vacuum. To the crude residue was added water (2 mL), followed by the addition of 6 M NaOH aqueous solution to adjust the pH 12-13. The reaction mixture was extracted with ethyl acetate (5 mL×3) and the separated organic layer was evaporated to provide free amine compound (1a) with yield (68 mg, 98%).

Example-4: (R)—N—((R)-2-(2-Methoxyphenyl)-1-(4-Methoxyphenyl)Ethyl)-2-Methylpropane-2-Sulfinamide (6d)

Charged 2.5 mL of tetrahydrofuran (THF) in a flask followed by the addition of ortho-methyl anisole (5a) (5.59 mmol) and n-butyl lithium (1.6 M in cyclohexane, 3.35 mmol) at a temperature of about 0° C. The reaction mixture was further cooled down to a temperature of about −78° C. and to the stirring solution was added N-tert-butanesulfinyl aldimine (3d) (200 mg, 1.11 mmol). The reaction mixture was continued for stirring for about 1 h at −78° C. temperature; followed by the dropwise addition of water (5 mL) at same temperature. The reaction mixture was extracted with ethyl acetate (5 mL×3) and the separated organic layer was evaporated to provide compound (6d) with yield (272 mg, 90%).

Example-5: (R)—N—((R)-2-(2-Methoxyphenyl)-1-(Thiophen-2-Yl)Ethyl)-2-Methylpropane-2-Sulfinamide (6f)

Charged 2.5 mL of tetrahydrofuran (THF) in a flask followed by the addition of ortho-methyl anisole (5a) (6.27 mmol) and n-butyl lithium (1.6 M in cyclohexane, 3.76 mmol) at a temperature of about 0° C. The reaction mixture was further cooled down to a temperature of about −78° C. and to the stirring solution was added N-tert-butanesulfinyl aldimine (3f) (200 mg, 1.25 mmol). The reaction mixture was continued for stirring for about 1 h at −78° C. temperature; followed by the dropwise addition of water (5 mL) at same temperature. The reaction mixture was extracted with ethyl acetate (5 mL×3) and the separated organic layer was evaporated to provide compound (6f) with yield (276 mg, 88%).

Example-6: (R)-2-(2-Methoxyphenyl)-1-Phenylethan-1-Amine (1″a)

Charged 0.7 mL of Dioxane in a flask followed by the addition of sulfinyl amine compound (6a) (100 mg, 0.28 mmol) and hydrochloric acid solution (4.0 M in dioxane, 2.8 mmol, 0.7 mL). The reaction mixture was stirred for 2 h at room temperature and the reaction mixture was concentrated under vacuum. To the crude residue was added water (2 mL), followed by the addition of 6 M NaOH aqueous solution to adjust the pH 12-13. The reaction mixture was extracted with ethyl acetate (5 mL×3) and the separated organic layer was evaporated to provide free amine compound (1″a) with yield (70 mg, 99%).

We claim:

1. A process for the preparation of a branched amine compound (1″) or a salt thereof; of the following formula,

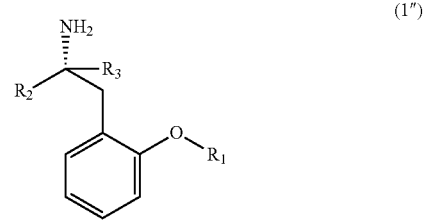

wherein, $R_1$, $R_2$ and $R_3$ are independently selected from H, $C_1$-$C_{10}$ linear or branched or cyclic alkyl, substituted or unsubstituted aryl, ester, ether, hetero aryl, halo, haloalkyl comprising the steps of;

(x) reacting substituted arene compound (5) of the following formula,

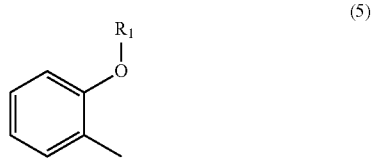

with N-tert-butanesulfinylimine compound (3) of the following formula,

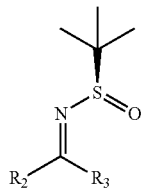
(3)

in the presence of a lithiating agent;
(y) removing the sulfinyl group from the compound sulfinyl amine (6) of stage (x) represented by the following formula,

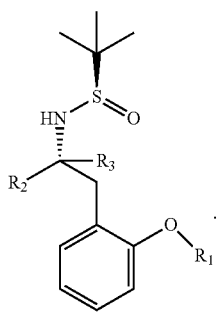
(6)

2. The process according to the claim 1, wherein the step (x) of claim 1 involves formation of cyclic lithiated compound (5-Li) of the following formula,

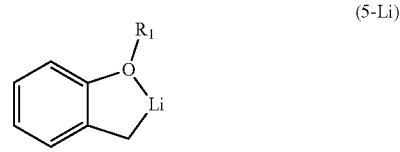
(5-Li)

wherein, $R_1$ is as defined herein.

3. The process according to the claim 1, wherein the lithiating agent used in step (x) of claim 1 is an organolithium compound selected from n-butyl lithium (n-BuLi), phenyllithium, methyllithium, tert-butyllithium or a mixture thereof.

4. The process according to the claim 1, wherein the step (y) of claim 1 involves the cleaving of the sulfinyl substitution of the amine by treatment of the sulfinyl amine compound (5) with an acid selected from hydrochloric acid, hydrobromic acid, hydrofluoric acid, nitric acid, sulfuric acid, phosphoric acid or a mixture thereof.

* * * * *